(12) United States Patent
Koulechov et al.

(10) Patent No.: US 8,596,272 B2
(45) Date of Patent: Dec. 3, 2013

(54) DEVICE FOR SEPARATING MOISTURE FROM BREATHING GAS

(75) Inventors: Kirill Koulechov, Niendorf (DE); Ralf-Jürgen Lange, Bad Schwartau (DE); Shuang Zhang, Stockelsdorf (DE)

(73) Assignee: Dräger Medical GmbH, Lübeck (DE)

( * ) Notice: Subject to any disclaimer, the term of this patent is extended or adjusted under 35 U.S.C. 154(b) by 746 days.

(21) Appl. No.: 12/700,284

(22) Filed: Feb. 4, 2010

(65) Prior Publication Data

US 2010/0199993 A1 Aug. 12, 2010

(30) Foreign Application Priority Data

Feb. 7, 2009 (DE) .......................... 10 2009 007 980

(51) Int. Cl.
  *A62B 7/00* (2006.01)
  *A62B 7/10* (2006.01)
  *A62B 23/02* (2006.01)

(52) U.S. Cl.
  USPC .................................. 128/205.27; 128/200.24

(58) Field of Classification Search
  USPC .......... 128/910, 914, 202.28–207.18; 96/118, 96/153
  See application file for complete search history.

(56) References Cited

U.S. PATENT DOCUMENTS

| | | | | |
|---|---|---|---|---|
| 3,800,516 A | * | 4/1974 | Paluch | ............................ 96/150 |
| 4,015,599 A | * | 4/1977 | Peterson | .................. 128/204.13 |
| 5,398,677 A | * | 3/1995 | Smith | ....................... 128/205.12 |
| 6,123,069 A | * | 9/2000 | Davis | ....................... 128/202.26 |
| 7,250,035 B1 | | 7/2007 | Ott et al. | |
| 2003/0167927 A1 | | 9/2003 | Ostberg | |
| 2008/0255531 A1 | * | 10/2008 | Ring et al. | ...................... 604/368 |

FOREIGN PATENT DOCUMENTS

GB   1 438 757 A   6/1976
WO   WO 01/83294 A1   11/2001
WO   WO 2009/006586 A2   1/2009

OTHER PUBLICATIONS

Förster, H.: Das Soda lime-Problem. In: Anaesthesist, 1999, vol. 48, No. 6, pp. 409-416, ISSN 1432-055X.

* cited by examiner

*Primary Examiner* — Nicholas Lucchesi
*Assistant Examiner* — Leah Stohr
(74) *Attorney, Agent, or Firm* — McGlew and Tuttle, P.C.

(57) ABSTRACT

A device (1) for separating moisture from breathing gas is improved in terms of the storage of water of condensation. A collection volume (5) is provided for water of condensation with a water-binding substance (6).

21 Claims, 2 Drawing Sheets

DEVICE FOR SEPARATING MOISTURE FROM BREATHING GAS

CROSS REFERENCE TO RELATED APPLICATIONS

This application claims the benefit of priority under 35 U.S.C. §119 of German Patent Application DE 10 2009 007 980.7 filed Feb. 7, 2009, the entire contents of which are incorporated herein by reference.

FIELD OF THE INVENTION

The present invention pertains to a device for separating moisture from breathing gas.

BACKGROUND OF THE INVENTION

Anesthesia systems are used to supply patients with breathing gas and volatile anesthetics. Respiration systems in which the breathing gas is circulated in a closed cycle and is again returned to the patient after removal of the expired carbon dioxide are usually used in anesthesia. Only the breathing gas consumed is replaced here.

Due to the circulation of the breathing gas in the closed breathing system, the breathing gas becomes enriched with moisture and water of condensation may be formed. So-called water traps, preferably in breathing tubes, are used to collect water of condensation, and these water traps must be checked and emptied at regular intervals. Disposal of water of condensation is not normally possible and would make handling of the anesthesia system difficult during the use of the device, which may sometimes continue over several days.

A disposable filter for cleaning expired gas is known from US 2003/0 167 927 A1. The filter is located in a filter housing, and the filter housing has a gas inlet and a gas outlet. A collection volume for water of condensation is located at the deepest point of the filter housing. The collection volume consists of transparent material and a color indicator is used to make it easier to monitor the filling level of the water of condensation in the collection container.

The drawback of the prior-art device is that water of condensation may flow back when the position of the inserted filter is changed when the collection volume is filled and water of condensation collects on the underside of the filter element.

SUMMARY OF THE INVENTION

The basic object of the present invention is to improve a device of the type mentioned in terms of the storage of water of condensation.

According to the invention, a device is provided for separating moisture from breathing gas. The device comprises a housing with a gas inlet and a gas outlet. A collection volume for water of condensation is provided on a side of the housing facing away from the gas inlet or the gas outlet. A water-binding substance is provided in the collection volume.

The water-binding substance may be present in the form of a powder or as a granular product. The water-binding substance may be absorbed by a carrier material such as a nonwoven.

The device may further comprise a filter material through which breathing gas flows. The filter material is arranged between the gas inlet and the gas outlet. The filter material may comprise material to adsorb carbon dioxide.

According to another aspect of the invention, a method of separating moisture from breathing gas is provided. The method comprises providing a housing with a gas inlet and a gas outlet, providing a collection volume for water of condensation on a side of the housing facing away from the gas inlet or the gas outlet, and providing a water-binding substance in the collection volume. The method includes passing gas into the gas inlet and out of the gas outlet to provide a water of condensation separator through which breathing gas flows or a carbon dioxide absorber to bind water of condensation.

Provisions are made according to the present invention for providing the collection volume for the water of condensation with a water-binding substance. It is especially advantageous here to use so-called superabsorbent polymers (SAPs), which have the ability to bind large quantities of water, as the water-binding substance. Superabsorbent polymers for binding liquid are known from hygienic articles and are available in various embodiments, for example, powders, granular products or even fibrous materials. SAP based on polyacrylic acid, which also includes crosslinked polyacrylic acid, polymers or copolymers, is of great significance. The properties of SAP are described by values of water storage capacity, rate of adsorption, permeability through liquids and gel stability. The water of condensation is absorbed by the use of the water-binding substance and there is no longer a risk that water of condensation would flow back into a filter element or back into a breathing tube system in case of a pure water of condensation separation.

It is especially advantageous to combine the water-binding substance with a carrier material. It is advantageous to prepare a mixture of, for example, cellulose with SAP or to surround SAP powder or granular SAP product with a nonwoven material. It is also possible to cover SAP powder or granular SAP product with nonwoven material.

A filter element arranged between the gas inlet and the gas outlet is advantageously designed as a carbon dioxide absorber, wherein the filter material is present in the form of so-called breathing lime based on calcium hydroxide. The water formed during the reaction of calcium hydroxide with carbon dioxide can be advantageously collected directly by means of the collection container located under the absorber and bound with the water-absorbing substance.

An advantageous use of a water-binding substance is the use of this substance in a water of condensation separator or in a carbon dioxide absorber.

An exemplary embodiment of the present invention is shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
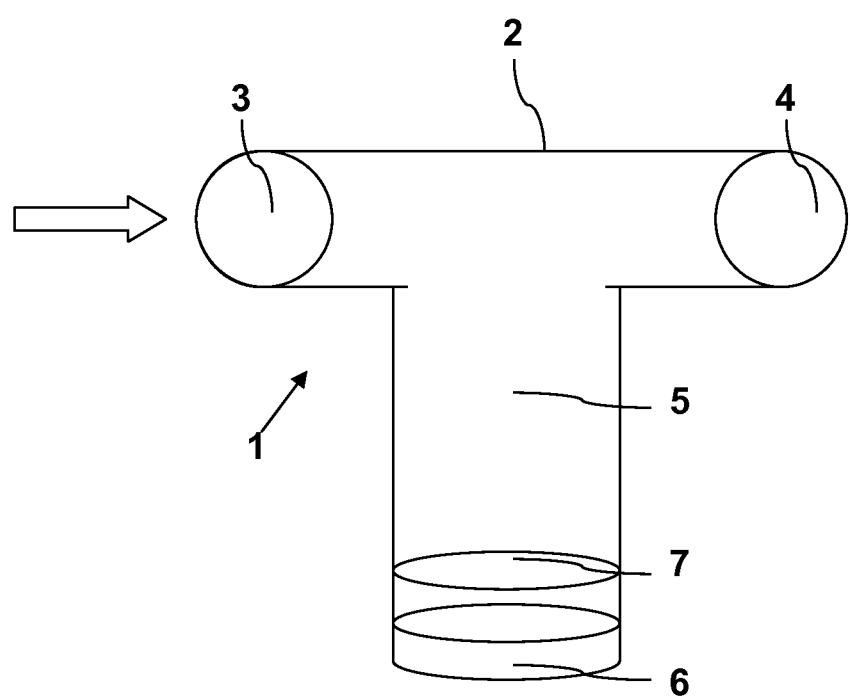
FIG. 1 is a water of condensation separator.

Referring to the drawings in particular, FIG. 1 schematically shows the design of a water of condensation separator 1 as it is usually used in respiration systems to remove water of condensation from lines carrying breathing gas. The water of condensation separator 1 has a housing 2 with a gas inlet 3 and with a gas outlet 4. On the side of housing 2 facing away from the gas inlet 3 and the gas outlet 4 is located a collection volume 5 for separated water of condensation. The collection volume 5 is provided in the lower area with a water-binding substance 6, preferably a superabsorbent polymer. Substance 6 is located under a nonwoven 7. Water of condensation separated from the breathing gas reaches substance 6 via the nonwoven 7 and is bound there. No liquid water of condensation can flow back to the gas inlet 3 or to the gas outlet 4 in case of a change in the position of the water of condensation separator 1.

Figure 2:
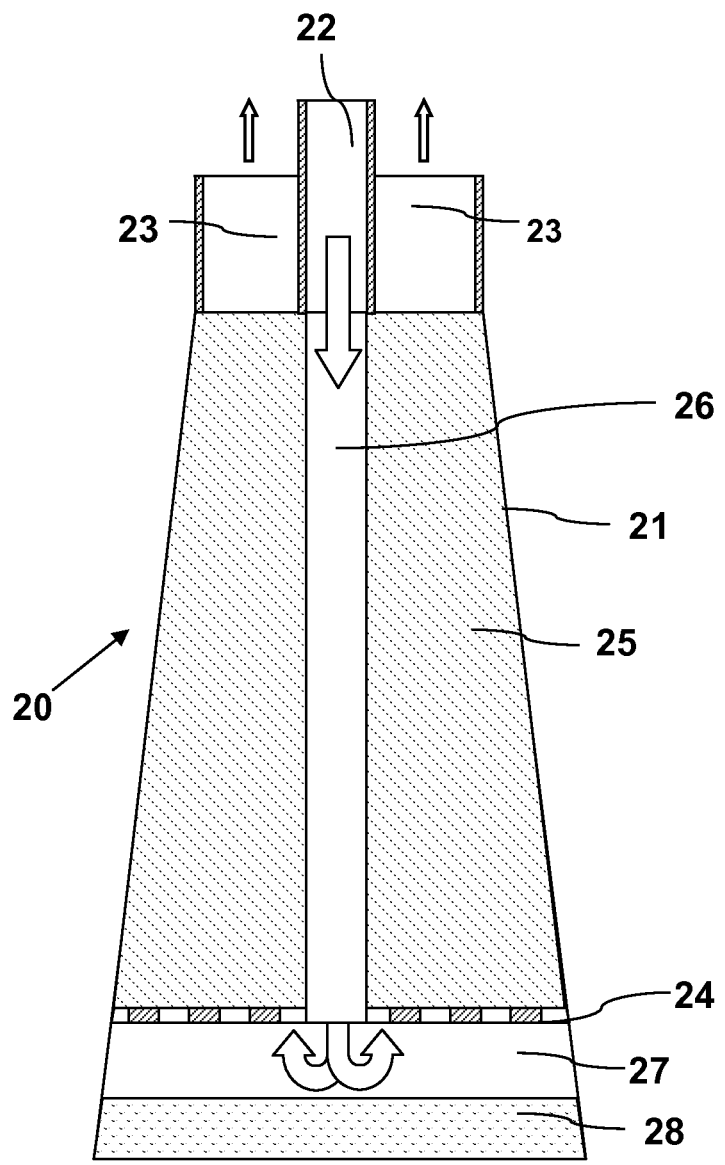
FIG. 2 is a carbon dioxide separator.

FIG. 2 illustrates a carbon dioxide absorber 20, in which a gas inlet 22 and a gas outlet 23 are provided in an absorber housing 21. Loose granular breathing lime 25 is located on a perforated plate 24 in the absorber housing 21. The breathing gas enters a collection volume 27 under the perforated plate 24 from the gas inlet 22 via a duct 26 arranged centrally in the absorber housing 21 and from there it reaches the gas outlet 23 via the perforated plate 24 and the breathing lime 25.

A layer of water-binding substance 28 in the form of a superabsorbent polymer, which collects and stores the water of condensation formed, is located in the lower area of the collection volume 27. Substance 28 prevents water of condensation from flowing back into the breathing lime 25.

While specific embodiments of the invention have been described in detail to illustrate the application of the principles of the invention, it will be understood that the invention may be embodied otherwise without departing from such principles.

APPENDIX

List of Reference Numbers

1 Water of condensation separator
2 Housing
3 Gas inlet
4 Gas outlet
5 Collection volume
6 Substance
7 Nonwoven
20 Carbon dioxide absorber
21 Absorber housing
22 Gas inlet
23 Gas outlet
24 Perforated plate
25 Breathing lime
26 Duct
27 Collection volume
28 Substance

What is claimed is:

1. A device for separating moisture from breathing gas, the device comprising:
   a housing with a breathing gas flow line connection side defining a gas inlet and a gas outlet and with a collection volume side spaced from the breathing gas flow line connection side;
   a collection volume for water of condensation within the housing on the collection volume side of the housing, facing away from said gas inlet and said gas outlet; and
   a water-binding substance in said collection volume.

2. A device in accordance with claim 1, wherein said water-binding substance is present in the form of a powder or as a granular product.

3. A device in accordance with claim 1, wherein said water-binding substance is a superabsorbent polymer.

4. A device in accordance with claim 1, wherein said water-binding substance is absorbed by a carrier material.

5. A device in accordance with claim 4, wherein said carrier material is a nonwoven material.

6. A device in accordance with claim 1, further comprising a filter material through which the breathing gas flows, said filter material being arranged between said gas inlet and said gas outlet.

7. A device in accordance with claim 6, wherein said filter material comprises material to adsorb carbon dioxide.

8. A method of separating moisture from breathing gas, the method comprising the steps of:
   providing a housing with a breathing gas flow line connection side defining a gas inlet and a gas outlet and with a collection volume side spaced from the breathing gas flow line connection side;
   providing a collection volume for water of condensation within the housing, on the collection volume side of the housing, facing away from said gas inlet and said gas outlet; and
   providing a water-binding substance in said collection volume.

9. A method in accordance with claim 8, further comprising passing gas into the gas inlet and out of the gas outlet to provide a water of condensation separator through which breathing gas flows or a carbon dioxide absorber to bind water of condensation.

10. A method in accordance with claim 9, wherein said water-binding substance is present in the form of a powder or as a granular product.

11. A method in accordance with claim 9, wherein said water-binding substance is a superabsorbent polymer.

12. A method in accordance with claim 9, wherein said water-binding substance is absorbed by a carrier material.

13. A method in accordance with claim 12, wherein said carrier material is a nonwoven.

14. A method in accordance with claim 9, further comprising providing a filter material through which the breathing gas flows, said filter material being arranged between said gas inlet and said gas outlet.

15. A method in accordance with claim 14, wherein said filter material comprises material to adsorb carbon dioxide.

16. A device for connection in a breathing gas flow line for separating moisture from breathing gas, the device comprising:
   a housing having a bottom end defining a liquid collection volume for water of condensation and having a top end defining a gas inlet, the gas inlet providing fluid communication between the breathing gas flow line and the collection volume and defining a gas outlet, the gas outlet providing fluid communication between the collection volume and the breathing gas flow line such that breathing gas flows into the gas inlet, into the collection volume and out of the gas outlet, the bottom end of the housing being spaced apart from the top end of the housing with the gas inlet and the gas outlet, at the top end spaced from the collection volume at the bottom end; and
   a water-binding substance in said collection volume.

17. A device in accordance with claim 16, further comprising a nonwoven fixed to the housing, the nonwoven being positioned in the housing between the water-binding substance and the gas inlet and the gas outlet, at the top end, for maintaining a position of said water-binding substance in said collection volume.

18. A device in accordance with claim 16, wherein said water-binding substance is a superabsorbent polymer.

19. A device in accordance with claim 16, further comprising:
   a breathing gas duct connected to the gas inlet and defining a breathing gas flow passage extending from the gas inlet, at the top end of the housing, to the collection volume;
   a filter space with a filter material through which the breathing gas flows, said filter space and said filter material being arranged within the housing, disposed spatially between the collection volume, at the bottom end, of the housing and said gas inlet and said gas outlet, at the top end of the housing and with respect to breathing gas flow, said filter space and said filter material being arranged downstream of the breathing gas duct and upstream of said gas outlet.

20. A device in accordance with claim 19, wherein said filter material comprises material to adsorb carbon dioxide whereby said device forms a carbon dioxide absorber which also binds water of condensation.

21. A device comprising:
   a housing having an end with a breathing gas flow line connection interface, the housing defining a collection volume for water of condensation spaced from the connection interface;
   a gas inlet at the connection interface, the gas inlet providing fluid communication between a breathing gas flow line and the collection volume;
   a gas outlet at the connection interface, the gas outlet providing fluid communication between the collection volume and the breathing gas flow line such that breathing gas flows into the gas inlet, into the collection volume and out of the gas outlet;
   a water-binding substance in said collection volume;
   an water-binding substance support, supporting the water-binding substance in the housing at a location in said collection volume;
   carbon dioxide absorber material in a path of the breathing gas;
   an absorber material support connected to the housing and supporting the carbon dioxide absorber material in the housing at a location spaced from the water-binding substance;
   a breathing gas flow duct connected to the gas inlet and defining a breathing gas flow passage extending from the gas inlet to the collection volume, the absorber material support being disposed downstream of the breathing gas duct whereby breathing gas flows in the inlet, through the breathing gas flow duct and into the collection volume, at which water of condensation is deposited and is bound to the water-binding substance in the collection volume, and breathing gas flows from the collection volume into the carbon dioxide absorber material and out of the housing through the outlet.

* * * * *